United States Patent [19]
Chang et al.

[11] Patent Number: 6,146,840
[45] Date of Patent: Nov. 14, 2000

[54] SIMULTANEOUS ENUMERATION OF *E. COLI* AND TOTAL COLIFORMS

[75] Inventors: George Chang; Rosalind Lum, both of Berkeley, Calif.

[73] Assignee: The Regents of the University of California, Oakland, Calif.

[21] Appl. No.: 08/235,488

[22] Filed: Apr. 29, 1994

[51] Int. Cl.[7] .................................................. C12Q 1/54
[52] U.S. Cl. ................................................ 435/14; 435/34
[58] Field of Search ................................. 435/14, 18, 29, 435/34, 38, 39, 25, 2.8, 253.6

[56] References Cited

U.S. PATENT DOCUMENTS

| | | | |
|---|---|---|---|
| 4,591,554 | 5/1986 | Koumura | 435/18 |
| 4,925,789 | 5/1990 | Edberg | 435/38 |
| 5,210,022 | 5/1993 | Roth | 435/34 |

OTHER PUBLICATIONS

"Dehydrated Culture Media and Reagents for Microbiology", *DIFCO Manual,* Tenth Edition, DIFCO Laboratories, Detroit, Michigan.
Atlas, "Handbook of Microbiological Media", CRC Press, Lawrence C. Parks (Ed.).
Rambach, "New Plate Medium for Facilitated Differentiation of Salmonella spp. from Proteus spp. and Other Enteric Bacteria", *Applied and Environmental Microbiology,* 56(1):301–303 (1990).
DIFCO Manual 10th Ed DIFCO Labs Detroit MI 1984 pp. 203–204.
Chang, G., Tactics for Combining the Coliform . . . J of Food Protection vol. 53 Oct. 1990 p. 910.
Chang, G., Tryptophaw & Gacactoside Media . . . Soc Microbiol 90(0) 1990 p. 290.
Bainbridge B., Improved Methods for the Detection . . . FEMS Micro Lett 80 (1991) pp. 319–324.
Atlas R., Handbook of Microbiological Media CRC Press FL pp. 132, 178.

*Primary Examiner*—Ralph Gitomer
*Attorney, Agent, or Firm*—Richard Aron Osman

[57] ABSTRACT

The general method involves contacting a bacterial colony with a β-D-galactosidase substrate and a carbon source metabolizable by a plurality of coliform species but not metabolizable by *E. coli,* and detecting reaction product signals of the substrate and carbon source. Typically, the carbon source is a carbohydrate, preferably adonitol, esculin, salicin, amygdalin, or cellobiose. The absence of both reaction product signals indicates the presence of non-coliform bacteria; the presence of both reaction product signals indicates the presence of non-*E. coli* coliform bacteria; and, the presence of the β-D-galactosidase substrate reaction product signal and absence of the carbon source reaction product signal indicates the presence of *E. coli.*

A signal may identify a reaction product itself (e.g. a colored product derived from a chromogenic form of the substrate or from a chromogenic reagent which interacts with the product, etc.), or an effect of a reaction product on or at the colony (e.g. catabolite repression, growth, localized pH change, etc.). Preferably, the β-D-galactosidase substrate reaction product signal is provided directly by a β-D-galactosidase reaction product and the carbon source reaction product signal is provided by carbon source reaction product-induced catabolite repression of the β-D-galactosidase substrate reaction product signal at a portion of the colony.

20 Claims, No Drawings

SIMULTANEOUS ENUMERATION OF E. COLI AND TOTAL COLIFORMS

FIELD OF THE INVENTION

The field of this invention is assays for characterizing bacterial colonies as coliform bacteria and specifically, E. coli.

BACKGROUND

Because of recent US-EPA rules, the traditional coliform test is no longer sufficient for water quality monitoring. One must now distinguish E. coli, the fecal indicator, from other coliforms that may grow as biofilms in water distribution systems. In recent years a number of tests for E. coli in drinking water have been developed. However, all these methods must be used in the cumbersome liquid fermentation format, either MPN tubes or in 100 ml presence-absence bottles. Because they are labor, material and time intensive, none of these are popular with test laboratories.

Membrane filtration is the overwhelming method of choice in water quality laboratories. However, a simple and economical membrane filter method for E. coli and total coliforms has never been developed. Even the method of Mates and Schaeffer (Membrane filtration differentiation of E. coli from coliforms in the examination of water, J. Appl. Bacteriol. 67, 343–346, 1989) requires two successive incubations on different media. This situation has forced the Millipore Corporation, the world's leader in membrane filter technology, to move away from filters and develop a liquid fermentation test for E. coli.

Public health and environmental monitoring would benefit enormously from a simple, inexpensive, one-step membrane-based test for enumerating E. coli and total coliforms.

Relevant Literature

Hensyl, et al. ed. Bergey's Manual of Determinative Bacteriology. 9th ed., particularly, pp. 202–289. Baltimore, Md.; Williams & Watkins 1994.

SUMMARY OF THE INVENTION

The invention provides methods and compositions for detecting coliform bacteria and E. coli. The general method involves contacting a bacterial colony with a β-D-galactosidase substrate and a carbon source metabolizable by a plurality of coliform species but not metabolizable by E. coli, and detecting reaction product signals of the substrate and carbon source. Typically, the carbon source is a carbohydrate, preferably adonitol, esculin, salicin, amygdalin, or cellobiose. The absence of both reaction product signals indicates the presence of non-coliform bacteria; the presence of both reaction product signals indicates the presence of non-E. coli coliform bacteria; and, the presence of the β-D-galactosidase substrate reaction product signal and absence of the carbon source reaction product signal indicates the presence of E. coli.

The reaction products result from the catalytic reaction of the indicator enzyme (e.g. β-D-galactosidase, β-glucosidase, etc.) and their respective substrates. The reaction products ultimately provide signals which may take a variety of forms, particularly a change in localized color or color intensity. A signal may identify a reaction product per se (e.g. a colored product or chromophore derived from a chromogenic form of the substrate or from a chromogenic reagent which interacts with the product, etc.), or an effect of a reaction product on or at the colony (e.g. catabolite repression, growth, localized pH change, etc.).

In one embodiment, the β-D-galactosidase substrate reaction product signal is provided directly by a β-D-galactosidase reaction product and the carbon source reaction product signal is provided by an effect of a carbon source reaction product on or at the colony. For example, X-Gal 5-bromo-4-chloro-3-indolyl-β-D-galactopyranoside provides a colored β-D-galactosidase substrate reaction product signal at the colony.

In this embodiment, the carbon source reaction product signal is provided by other than a colored product or chomophore produced by a chromogenic substrate or chromogenic reagent which interacts with a reaction product. Frequently this signal is provided by a change in metabolism of at least a portion of the colony (e.g. catabolite repression, growth, etc.) or a downstream metabolic product ultimately generated by or in response to the carbon source (e.g. pyruvate, hydrogen ions, etc). This signal may be detected by comparing two distinguishable regions of the bacterial colony: a first core region and a second region located outwardly of said first region. For example, the carbon source reaction product signal can manifest itself as a lower intensity β-D-galactosidase reaction product signal, a lower localized pH, or a higher localized reductive metabolite (e.g. NADH, NADPH, etc.) concentration at the second region as compared with the first region. The localized pH and reductive metabolite concentration are conveniently detected indirectly with reagents, such as a pH indicator or tetrazolium dye, respectively. Reagents and/or incubation conditions which enhance the signal reaction product signal difference between the first and second regions are disclosed.

Optionally, the method may be combined with other confirmatory enzymatic tests. For example, tryptophanase activity can affirmatively distinguish E. coli from other coliforms. In this example, the bacterial colony would be additionally contacted with a tryptophanase substrate and a tryptophanase reaction product detected at the colony. A preferred tryptophanase substrate, tryptophan, provides indole as a reaction product which may be detected with a reagent such as p-dimethylaminobenzaldehyde.

The disclosed methods are useful with a wide variety of samples, particularly water samples. The method is conveniently practiced on a solid or semisolid substrate such as a microporous filter. A wide variety of base media and incubation conditions may be used. Significantly, the methods may be performed at ambient temperature. The invention also provides sterile media and kits adapted to the disclosed methods for use in detecting coliform bacteria and E. coli.

DESCRIPTION OF SPECIFIC EMBODIMENTS

The invention provides methods and compositions for detecting coliform bacteria and E. coli in a wide variety of samples. Virtually any sample suspected of coliform contamination can be tested, including food, clinical, environmental and industrial samples. The method has been validated in comparison to EPA protocols.

The method is specifically adapted to testing isolated bacterial colonies. The invention is generally practiced on (including within) a solid or semisolid substrate such as agar, a microporous filter, etc. The bacteria may be isolated from the sample in any convenient manner. For example, a water sample may be directed through a microporous filter which retains bacteria and the filter placed in contact with a nutrient medium, usually semisolid, for incubation. The method is particularly suited to testing water samples with highly dilute microbial presence; the test volumes being limited only by the amount of sample that can be passed throught a microporous filter. With samples low in particulate matter for example, the method effectively determines the presence of fewer than one coliform per ten liters.

The isolated bacteria may be grown into colonies in any convenient manner. Colonies to be tested may be of any size detectable by light microscopy, though the method is more conveniently practiced with colonies easily detected by dissecting microscope or the unaided eye. Generally, assayed colonies are at least about 0.05, preferably at least about 0.25, more preferably at least about 1 mm in diameter.

The general method involves exposing the colonies to a β-D-galactosidase substrate and a carbon source metabolizable by a plurality of coliform species but not metabolizable by *E. coli*. In essence, coliforms are identified by β-D-galactosidase activity and *E. coli* are identified as coliforms unable to metabolize the forementioned carbon source. More specifically, the absence of both β-D-galactosidase substrate and carbon source reaction products indicates the presence of non-coliform bacteria; the presence of both reaction products indicates the presence of non-*E. coli* coliform bacteria; and, the presence of the β-D-galactosidase substrate reaction product and absence of the carbon source reaction product signal indicates the presence of *E. coli*. In addition, the general method may be supplemented with an affirmative test for an enzymatic activity specific to *E. coli* among coliforms.

The carbon source metabolizable by a plurality of coliform species but not metabolizable by *E. coli* may take a wide variety of forms, e.g. carbohydrates, amino acids, etc. To minimize false positives, the carbon source should not be detectably metabolized in the subject assay by those *E. coli* strains likely to be present in the sample. To minimize false negatives, the carbon source is selected to be metabolizable by as many as possible non-*E. coli* coliforms that are likely to present in the sample. For example, in many samples, especially water samples, common non-*E. coli* coliforms include strains of *Klebsiella, Citrobacter* and *Enterobacter*. The carbohydrates adonitol, esculin, salicin, amygdalin, and cellobiose are shown to be particularly effective at identifying coliforms and distinguishing *E. coli* in a wide variety of isolates. An optimal carbon source is readily selected using the above criteria, reaction product signal strength, comparison with other coliform detection tests, e.g. mEndo agar or mTEC supplemented with a urease or glucuronidase test, cost and availability, etc.

The enzyme reaction products may be detected directly, indirectly or inferentially, by any convenient means. The choice of detection means is dictated by factors such as ease of detection, speed, cost, compatibility with the overall method including microbial growth, etc. Detection of a reaction product per se by visible color changes at the subject colony is often an efficient method with minimal equipment requirements. Direct detection means that an indicator enzyme reaction product per se is detected, indirect means that a different compound which interacts with a reaction product is detected, while inferentially means that the reaction product provides a signal by its effect on at least some of the bacteria in the colony, by interacting with another reagent, etc. Preferred reaction products provide maximal signal to noise ratio: a maximally detectable signal at the producing colony and minimal signal away from the colony. For example, the diffusion of a reaction product from the colony is preferably restrained, e.g. the product is preferably insoluble under the assay conditions or the product binds the solid substrate. As examples, a number of β-D-galactosidase substrates, such as X-Gal, provide a colored insoluble reaction product. Such chromogenic substrate-indicators are available or readily produced for many diagnostic enzymes.

Indirect detection is often more cost-effective, and the products of a wide variety of enzymes may be detected with product-specific reagents. Especially where the substrate is a primary, abundant or preferred carbon source, general metabolic products such as respirative or fermentive intermediates (e.g. acetate, acidity), growth or growth rate, utilization or depletion of a media component, or another indicia of nutritive state (e.g. membrane potential) may provide suitable reaction product signals of the carbon source. Such signals may be directly detectable (e.g. colony size) or require additional reagents to generate a detectable signal (e.g. pH indicators or tetrazolium dyes are used to detect acidity (hydrogen ion concentration) or reductive metabolites, respectively, at a colony).

In particular, the carbon source reaction product signal is frequently detected as an effect on the metabolism of at least a portion of the colony. For example, the bacterial colony can comprise two distinguishable regions: a first core region and a second annular region located outwardly of said first region. The carbon source reaction product signal can manifest itself as a lower intensity first reaction product signal and/or a lower localized pH and/or higher reductive metabolite concentration, at the second region as compared with the first region. The difference between the regions is likely due to the greater exposure of the outer region, and hence the bacteria therein, to the carbon source. By metabolizing a greater amount of the carbon source, these microbes frequently repress metabolic pathways of less favored nutrients (e.g. by catabolite repression). Thus, the repression of a less favored metabolic enzyme may be detected as a carbon source reaction product signal or contribute thereto. For example, the signal may be provided by a reduction in the β-D-galactosidase reaction product signal as compared with the first, inner region, or signal reduction provided by a different enzyme reaction product (e.g. indole). In these embodiments, *E. coli* colonies will have a relatively uniform expression of the β-D-galactosidase reaction product and non-*E. coli* coliforms (e.g. *Klebsiella*), will have a core expressing the β-D-galactosidase product surrounded by a ring of carbon source reaction product expression.

Where the carbon source signal is detected in reference to inner and outer colony regions, the regions may be of any size detectable by light microscopy, though the method is more conveniently practiced with regions easily detected by dissecting microscope or the unaided eye. Generally, the inner regions should be at least about 0.025, preferably at least about 0.1, more preferably at least about 0.5 mm in diameter, and the outer region at least about 0.025, preferably at least about 0.1, more preferably at least about 0.5 mm thick. Where the signal is outer region enzyme repression, the outer region will typically present no more than 75%, preferably no more than 50%, more preferably no more than about 25% of the inner region signal intensity.

Reagents and/or incubation conditions which enhance the reaction product signal difference between the first and second regions are disclosed. For example, repression of the production of β-D-galactosidase reaction product may be enhanced by contacting the colony with yet another carbon source (e.g. glucose, pyruvate, etc.) which is metabolizable by at least the non-*E. coli* coliforms, though often this carbon source will be metabolizable by many coliforms including *E. coli*. Accordingly, this carbon source is selected to synergistically repress β-D-galactosidase activity in conjunction with the non-*E. coli* specific substrate. Furthermore, the concentration must be strictly limited to maximize repression at non-*E. coli* colonies and minimize repression at *E. coli* colonies.

Other reagents and/or incubation conditions that limit bacterial growth by means other than limiting carbon source availability and/or promoting an intracellular accumulation of carbon source may enhance first and second region signal differences. Exemplary reagents include poisons such as respiratory poisons or semitoxic dyes (e.g. azide, cyanide, crystal violet), antibiotics (e.g. nalidixic acid, chloramphenicol), urea, guanidine. Exemplary conditions include starvation for nitrogen (e.g. tryptose, ammonium), phosphate, salts, etc.

Optionally, the method may be combined with other confirmatory enzymatic tests. For example, typtophanase activity can affirmatively distinguish *E. coli* from other coliforms. In this example, the bacterial colony would be additionally contacted with a tryptophanase substrate (e.g. tryptophan) and a tryptophanase reaction product (e.g. indole) detected at the colony (e.g. with an indole detection reagent like p-dimethylaminobenzaldehyde). The presence of the tryptophanase reaction product then affirmatively confirms the presence of *E. coli* in the colony. In this example, it is important to repress indole production in non-*E. coli* cells which may be present in the sample. For examples, high temperature incubations (between 44.3 and 44.7° C.) for at least one, preferably between about three and 24 hours), or reagents that preferentially cause or enhance catabolite repression of tryptophanase in the non-*E. coli* coliforms. Examples of such reagents include nutrients, including carbon sources, that are favorably and preferentially metabolized by the non-*E. coli* coliforms, e.g. adonitol, cellobiose, etc.

The disclosed methods are useful with a wide variety of samples, particularly water samples. The method is conveniently practiced on a solid or semisolid substrate such as a microporous filter. A wide variety of base media and incubation conditions may be used. Significantly, the methods may be performed at ambient temperature. The invention also provides sterile media and kits adapted to the disclosed methods for use in detecting coliform bacteria and *E. coli*. Such media often includes reagents to restrict the growth of gram positive bacteria, such as detergents and detergent-like compounds (e.g. sodium lauryl sulfate, bile salts, tergitol 7) and gram positive specific antibiotics (e.g. monensin, penecillin, etc.).

The method may be adapted to a wide variety of incubation conditions and base media. See, the Difco Catalog and U.S. patent application Ser. No. 08/091,528 filed Jul. 12, 1993 U.S. Pat. No. 5,411,867 which a continuation of 07/887,471 filed May 22, 1992, which is a continuation in part of 07/523,320 filed Mar. 14, 1990 which describe a variety of media and media components (e.g. β-D-galactosidase inducers like IPTG, etc.) which find use herein. For example, methods to facilitate recovery of chlorine injured cells with pyruvate, TMAO, etc., may be used in conjunction with the present invention.

The invention also provides sterile media and kits adapted to the disclosed methods for use in detecting coliform bacteria and *E. coli*. Typically, the kits include premeasured amounts of the disclosed substrates and support media such as semi-solid agar or microporous filters for growing sample-derived colonies.

The following examples are offered by way of illustration and not by way of limitation.

EXAMPLES

Media comprising a β-D-galactosidase substrate and a carbon source metabolizable by a plurality of coliform species but not metabolizable by *E. coli* are referred to as mX media. A wide variety of base media, usually providing salts, buffers and a general nutrient, have been tested as mX formulations.

I. General procedure for mX Experiments:
Bacterial dilutions

*E. coli* ATCC 25922, *Citrobacter freundii* ATCC 8090, and *Klebsiella pnuemoniae* TC 249 were used as control strains in all experiments. Nutrient broth cultures of control strains were grown at 35° C. for 18–24 hours. Strains were then diluted 10 in 0.9% saline immediately before membrane filtration.

Membrane filtration 0.1 ml of a $10^{-6}$ dilution of each control strain was swirled with about 20 ml of sterile saline in a presterilized filter holder apparatus (Nalgene 310). The resulting bacterial suspensions were then vacuum filtered through a sterile cellulose nitrate membrane filter (0.45 mm Gelman GN-6 or Millipore 0.7 mm HCWG). Membrane filters were then carefully transferred to mX agar plates. Plates were incubated 35° C. for 18–24 hours, and colony appearance was observed using either ordinary fluorescent or incandescent light, both with and without the aid of a dissecting microscope ( 7–30 x) (American optical).

Field validation: sewage sample 0.1 ml aliquots of a $10^{-6,}$ $10^{-5}$, and $10^{-4}$ diluted primary sewage influent sample were sequentially mixed with about 20 ml of sterile saline each in a presterilized filter holder apparatus (Nalgene 310). Aliquots were vacuum filtered and membrane filters were subsequently incubated on MacConkey-mX medium using the same procedure described above for the control strains. Representative colonies of differing appearance were selected for purification and identification using the API20E system (Sherwood Medical).

II. MacConkey based mX medium

MacConkey agar (Difco), a commonly used agar for the isolation of enterobacteriacae, was used as a medium base in initial trials. We compared the appearance of colonies of laboratory control *E. coli* and coliform strains on modified MacConkey-mX agar to the appearance of colonies produced by naturally occurring bacteria in primary sewage influent.

40 g Difco brand MacConkey agar base, 50 mg XGal predissolved in 0.1 ml dimethylformamide, 5 g adonitol, 5 g cellobiose, and 0.1 g IPTG were dissolved in 1 liter of distilled water. The medium was sterilized at 121° C., 15 p.s.i. for 15 minutes, and then poured into pre-sterilized 45 mm petri dishes, and allowed to solidify. Plates were refrigerated (4–7° C.) until use.

Colony appearance of *E. coli* ATCC 25922 and naturally occurring sewage influent bacteria on MacConkey-mX medium

| Origin of strain | Colony appearance | Bacterial identification |
| --- | --- | --- |
| primary sewage influent | dark blue center, colorless outer region | *Citrobacter freundii* |
| primary sewage influent | light blue center, white outer region | *Vibrio fluvialis* |
| primary sewage influent | pink center, white outer region | *Aeromonas hydrophila* |
| primary sewage influent | green center, white outer region | *Aeromonas hydrophila* |
| primary sewage influent | yellow only | *Aeromonas hydrophila* |
| primary sewage influent | white only | *Pasteurella multicida* |

-continued

| Origin of strain | Colony appearance | Bacterial identification |
|---|---|---|
| American Type Culture Collection Reference Strain | Dark blue only | *E. coli* ATCC 25922 |
| Laboratory strain | blue center, white outer region | *Klebsiella oxytoca* |

*Citrobacter* colonies had a slightly broader colorless zone at their periphery, which was visible with the dissecting microscope. Additionally, other agar bases, 30 e.g. Colitag base, produce a larger colorless colony border region. We have also found that a low level of glucose, such as 0.15%, allows for a bigger colony and better development of the pale-colored outer region, enhancing the distinct "bullseye" appearance to non-*E. coli* coliform colonies. Low levels of nalidixic acid, antibiotic, or detergent such as sodium lauryl sulfate are found to inhibit the growth of other interfering non-coliforms.

III. Nutrient broth based mX medium

To get a more intense red color development in the outer region of the coliform colonies, we switched our agar base to nutrient agar (Difco). Unlike MacConkey agar base, nutrient agar contains no pH indicators or dyes in its formulation. This allowed us to experiment with different dyes, dye concentrations, and dye combinations. Media variations tested include:

Nutrient broth based mX medium 1/1a 8 g nutrient broth, 15 g agar, 8 g sodium chloride, 0.05/0.07 g neutral red, 50 mg XGal predissolved in 0.1 ml dimethylformamide, 5 g adonitol, 5 g cellobiose, and 0.1 g IPTG were dissolved in 1 liter of distilled water. The medium was sterilized at 121° C. and 15 p.s.i. for 15 minutes and then poured into pre-sterilized 45 mm petri dishes, and allowed to solidify.

Nutrient broth based mX medium 2

8 g nutrient broth, 15 g agar, 8 g sodium chloride, 0.04 g brilliant yellow, 50 mg XGal predissolved in 0.1 ml dimethylformamide, 5 g adonitol, 5 g cellobiose, and 0.1 g IPTG were dissolved in 1 liter of distilled water. The medium was sterilized at 121° C. and 15 p.s.i. for 15 minutes and then poured into pre-sterilized 45 mm petri dishes, and allowed to solidify.

Nutrient broth based mX medium 3

8 g nutrient broth, 15 g agar, 8 g sodium chloride, 0.04 g phenol red, 50 mg XGal predissolved in 0.1 ml dimethylformamide, 5 g adonitol, 5 g cellobiose, and 0.1 g IPTG were dissolved in 1 liter of distilled water. The medium was sterilized at 121° C. and 15 p.s.i. for 15 minutes and then poured into pre-sterilized 45 mm petri dishes, and allowed to solidify.

Nutrient broth based mX medium 4

8 g nutrient broth, 15 g agar, 8 g sodium chloride, 0.04 g alizarin, Cl, 50 mg XGal predissolved in 0.1 ml dimethylformamide, 5 g adonitol, 5 g cellobiose, and 0.1 g IPTG were dissolved in I liter of distilled water. The medium was sterilized at 121° C. and 15 p.s.i. for 15 minutes and then poured into pre-sterilized 45 mm petri dishes, and allowed to solidify.

Nutrient broth based mX medium 5a–5l 8 g nutrient broth, 15 g agar, 8 g sodium chloride, 0.04 g bromothymol blue, 50 mg XGal predissolved 0.1 ml in dimethylformamide, 5 g adonitol, 5 g cellobiose, and 0.1 g IPTG were dissolved in I liter of distilled water. Acidity was not adjusted and adjusted to pH 6.2–7.2, in 0.1 increments, for 5a–5l, respectively. The medium was sterilized at 121° C. and 15 p.s.i. for 15 minutes and then poured into pre-sterilized 45 mm petri dishes, and allowed to solidify.

Nutrient broth based mX medium 6a–6f 8 g nutrient broth, 8 g sodium chloride, 0.06 g brilliant yellow, 50 mg XGal predissolved in 0.1 ml dimethylformamide, 5 g adonitol, 5 g cellobiose, and 0.1 g IPTG were dissolved in 1 liter of distilled water. Acidity was adjusted to pH 6.2–7.2, in 0.2 increments for 6a–6f, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

Nutrient broth based mX medium 7a–7f 8 g nutrient broth, 8 g sodium chloride, 0.06 g neutral red, 50 mg XGal predissolved in 0.1 ml dimethylformamide, 5 g adonitol, 5 g cellobiose, and 0.1 g IPTG were dissolved in 1 liter of distilled water. Acidity was adjusted to pH 6.2–7.2, in 0.2 increments for 7a–7f, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

III. Colitag based mX media

Nutrient agar allowed all our control strains to grow sufficiently on membrane filters. To improve color development, we used a Colitag base for mX media, which produced larger colonies and improved color differentiation in the colony border region. Favorable results were obtained so a Colitag base was used for mX media experiments below, unless otherwise indicated. The table below shows the colony appearances of our control *E. coli* and *K. pneumoniae* strains after 18–24 hours at 35° C. on mX agar with various pH indicators. Data below is a summary representing over 400 observations.

Colony appearance of *E. coli* and *K. pnuemoniae* on mX Colitag agar with various pH indicators

| pH indicator[1] | Colony appearance of *E. coli* ATCC 25922 | Average colony size | Colony appearance of *Klebsiella pnuemoniae*[2] TC 249 | Average colony size |
|---|---|---|---|---|
| neutral red | dark-blue only | 1 mm | light-blue center, large light-red outer region | 2 mm |
| brilliant yellow | dark-green only, yellow filter[3] | 1 mm | green center, large yellow outer region, yellow filter[3] | 2 mm |
| bromothymol blue | blue-green only, yellow filter[3] | 1 mm | green center, large pale yellow colored outer region, yellow filter[3] | 2 mm |
| alizarin | blue only | 0.5 mm | almost colorless | 2 mm |
| propyl red | blue only, pink-orange filter[3] | 1 mm | light-blue center, large pale orange outer region, pink-orange filter[3] | 2 mm |
| phenol red | blue only | 1 mm | light-blue center, large white-colored outer region | 2 mm |
| bromothymol blue + indigo carmine (0.02 g/l) | dark green only, on light green filter[3] | 1 mm | light-green center, large pale yellow outer region, yellow filter[3] | 2 mm |
| bromothymol blue + evans blue 0.009 g/l) | dark blue-green only, green filter[3] | 1 mm | light-green center, large, pale yellow-green |  |

-continued

| pH indicator[1] | Colony appearance of E. coli ATCC 25922 | Average colony size | Colony appearance of Klebsiella pnuemoniae[2] TC 249 | Average colony size |
|---|---|---|---|---|
| bromothymol blue + propyl red (0.03 g/l) | dark green only, pink filter[3] | 1 mm | outer region, green filter[3] light-green center, large, pale yellow outer region, red filter[3] | 2 mm |

[1]The concentration of pH indicators was between 0.04–0.06 g/l unless otherwise specified. Initial pH of agar was 7.0–7.2.
[2]A commonly occurring coliform.
[3]Membrane filters were colored by some pH indicators.

In previous studies, we have concentrated on developing improved media for recovery of chlorine injured *E. coli* (USEPA protocol; USEPA protocol to validate new *E coli* or coliform test methods: "Requirements for Nationwide Approval of New or Optionally Revised Methods for Total Coliforms, Fecal Coliforms, and *E. coli* in National Primary Drinking Water Regulations Monitoring." Aug. 19, 1991, Revised Jul. 9, 1992). During this process, we discovered the technique of proton gradient resuscitation. This method involves temporary acidification of the extracellular environment, allowing bacteria with damaged cell membranes to maintain a transmembrane proton gradient necessary for various metabolic processes. We performed several variable pH experiments to determine an optimal initial pH for mX media. We found that among nutrient broth grown control strains, pH did not largely affect colony color or size. Similar results are obtained in pH experiments on chlorine injured bacteria cells. Some results are listed in the tables below.

Colony appearance of *E. coli* and *K. pnuemoniae* on mX agar with various pH indicators

| pH indicator[1] | Initial pH | Colony appearance of E. coli ATCC 25922 | Average colony size | Colony appearance of Klebsiella pnuemoniae[2] TC 249 | Average colony size |
|---|---|---|---|---|---|
| neutral red | 6.0 | dark-blue only | 1 mm | light blue center, light red outer region | 2 mm |
| neutral red | 6.3 | dark-blue only | 1 mm | light blue center, light red outer region | 2 mm |
| neutral red | 6.4 | dark-blue only | 1 mm | light blue center, light red outer region | 2 mm |
| neutral red | 6.6 | dark-blue only | 1 mm | light blue center, light red outer region | 2 mm |
| neutral red | 6.8 | dark-blue only | 1 mm | light blue center, light red outer region | 2 mm |
| neutral red | 7.0 | dark-blue only | 1 mm | light blue center, light red outer region | 2 mm |
| neutral red | 7.2 | dark-blue only | 1 mm | light blue center, light red outer region | 2 mm |
| brilliant yellow | 6.4 | dark green only | 1 mm | light green center, light yellow outer region | 2 mm |
| brilliant yellow | 6.6 | dark green only | 1 mm | light green center, light yellow outer region | 2 mm |
| brilliant yellow | 6.8 | dark green only | 1 mm | light green center, light yellow outer region | 2 mm |
| brilliant yellow | 7.0 | dark green only yellow filter[3] | 1 mm | light green center, light yellow outer region | 2 mm |
| brilliant yellow | 7.2 | dark green only yellow filter[3] | 1 mm | light green center, light yellow outer region | 2 mm |
| bromothymol blue | 6.0 | blue only, yellow filter[3] | 1 mm | green center, large pale-yellow outer region, yellow filter[3] | 2 mm |
| bromothymol blue | 6.2 | blue only, yellow filter[3] | 1 mm | green center, large pale-yellow outer region, yellow filter[3] | 2 mm |
| bromothymol blue | 6.4 | blue only, yellow filter[3] | 1 mm | green center, large pale-yellow outer region, yellow filter[3] | 2 mm |
| bromothymol blue | 6.6 | blue only, yellow filter[3] | 1 mm | green center, large pale-yellow outer region, yellow filter[3] | 2 mm |
| bromothymol blue | 6.8 | blue only, yellow filter[3] | 1 mm | green center, large pale-yellow outer region, yellow filter[3] | 2 mm |
| bromothymol blue | 7.0 | blue only, yellow filter[3] | 1 mm | green center, large pale-yellow outer region, yellow filter[3] | 2 mm |
| bromothymol blue | 7.2 | blue only, yellow filter[3] | 1 mm | green center, large pale-yellow outer region, yellow filter[3] | 2 mm |
| phenol red | 6.0 | blue only | 1 mm | light-blue center, large colorless outer region | 2 mm |
| phenol red | 6.3 | blue only | 1 mm | light-blue center, large colorless outer region | 2 mm |
| phenol red | 6.6 | blue only | 1 mm | light-blue center, large colorless outer region | 2 mm |

-continued

| pH indicator[1] | Initial pH | Colony appearance of E. coli ATCC 25922 | Average colony size | Colony appearance of Klebsiella pnuemoniae[2] TC 249 | Average colony size |
|---|---|---|---|---|---|
| phenol red | 7.0 | blue only | 1 mm | light-blue center, large colorless outer region | 2 mm |

[1]The concentration of pH indicators was between 0.04–0.06 g/l unless otherwise specified. Initial pH of agar was 7.0–7.2.
[2]A commonly occurring coliform.
[3]Membrane filters were colored by some pH indicators.

Tested mX media formulations mX medium 1a–1d 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.04 g neutral red were dissolved in 1 liter of distilled water. Acidity was adjusted to pH 6.3, 6.6, 7.0 and 7.2, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 2a–2g 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g neutral red were dissolved in 1 liter of distilled water. Acidity was adjusted to pH 6.0–7.2, in 0.2 increments, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 3a–3c 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.08 g neutral red were dissolved in 1 liter of distilled water. Acidity was adjusted to pH 6.6, 7.0 and 7.2, respectively. 15 g of agar was added and dissolved with constant stirring and heat. The medium was sterilized at 121C and 15 p.s.i. for 15 minutes and then poured into pre-sterilized 45 mm petri dishes, and allowed to solidify.

mX medium 4a–4f 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g brilliant yellow were dissolved in 1 liter of distilled water. Acidity was adjusted to pH 6.2–7.2, in 0.2 increments, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 5a–5e 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g bromothymol blue were dissolved in 1 liter of distilled water. Acidity was adjusted to pH 6.0, 6.3, 6.6, 7.0 and 7.2, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 5f–5g 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.04 g bromothymol blue were dissolved in 1 liter of distilled water. Acidity was adjusted to pH 7.0 and 7.2, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 6a–6c 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.08 g bromothymol blue were dissolved in 1 liter of distilled water. Acidity was adjusted to pH 6.6, 7.0 and 7.2, respectively 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 7a–7e 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g propyl red were dissolved in 1 liter of distilled water. Acidity was adjusted to pH 6.0, 6.3, 6.6, 7.0 and 7.2, respectively. 15 g of agar was added and dissolved with constant stirring and heat. The medium was sterilized at 121° C. and 15 p.s.i. for 15 minutes and then poured into pre-sterilized 45 mm petri dishes, and allowed to solidify.

mX medium 8

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g propyl red, and 15 g agar were dissolved in 1 liter of distilled water. The medium was sterilized at 121° C. and 15 p.s.i. for 15 minutes and then poured into pre-sterilized 45 mm petri dishes, and allowed to solidify.

mX medium 9

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 0.06 g alizarin, and 15g agar were dissolved in 1 liter of distilled water. The medium was sterilized at 121° C. and 15 p.s.i. for 15 minutes and then poured into pre-sterilized 45 mm petri dishes, and allowed to solidify.

IV. Variable background dyes with bromothymol blue base dye

We found that a second pH indicator or dye added into mX media could color the cellulose nitrate membrane filter, providing better visual contrast against the pale-colored outer region of coliform colonies. In our latest formulations, we usually add 2 dyes into mX media for this purpose.

mX medium 10

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, 0.06 g bromothymol blue, 0.02 g indigo carmine, and 15 g agar were dissolved in 1 liter of distilled water. The medium was sterilized at 121° C. and 15 p.s.i. for 15 minutes and then poured into pre-sterilized 45 mm petri dishes, and allowed to solidify.

mX medium 11

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, 0.06 g bromothymol blue, 0.04 g propyl red, and 15 g agar were dissolved in 1 liter of distilled water. The medium was sterilized at 121° C. and 15 p.s.i. for 15 minutes and then poured into pre-sterilized 45 mm petri dishes, and allowed to solidify.

mX medium 12

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, 0.06 g bromothymol blue, 0.009 g evans blue, and 15 g agar were dissolved in 1 liter of distilled water. The medium was sterilized at 121° C. and 15 p.s.i. for 15 minutes and then poured into pre-sterilized 45 mm petri dishes, and allowed to solidify.

V. Variable tryptose

A variable tryptose experiment was performed to determine the optimal concentration range for tryptose in mX media. The experiment demonstrated that colonies are unlikely to grow to be 1 mm or larger in the absence of tryptose. Development of characteristic colony colors is impaired at very low tryptose concentrations. This effect is likely due to increased bacterial growth and colony development which occurs with tryptose supplementation. Results for colony appearance and colony size are listed in the tables below.

Effect of tryptose concentration on colony appearance

| Percent tryptose | E. coli ATCC 25922 | K. pnuemoniae TC 249 | C. freundii ATCC 8090 |
| --- | --- | --- | --- |
| 0.0 | blue only | colorless | nvg[1] |
| 0.2 | dark blue only | Light green center, pale colored outer region | light blue center, white outer region |
| 0.6 | dark blue only | Light green center, pale colored outer region | light blue center, white outer region |
| 0.8 | dark blue only | Light green center, pale colored outer region | light blue center, white outer region |
| 1.0 | dark blue only | Light green center, pale colored outer region | light blue center, white outer region |

Effect of tryptose concentration on colony size

| Percent tryptose | E. coli ATCC 25922 | K. pnuemoniae TC 249 | C. freundii ATCC 8090 |
| --- | --- | --- | --- |
| 0.0 | visible[2] | visible[2] | nvg[1] |
| 0.2 | 1 mm | 2 mm | 0.5 mm |
| 0.6 | 2 mm | 2–3 mm | 1 mm |
| 0.8 | 2 mm | 2–3 mm | 1 mm |
| 1.0 | 2 mm | 2–3 mm | 1 mm |

[1]No visible growth.
[2]Visible with dissecting scope, but too small to measure.

Variable Tryptose Media
mX medium 13a–e 50 mg XGal predissolved in 0.1 ml dimethylformamide, 0.1 g IPTG, 5 g adonitol, 5 g cellobiose, 2.9 g sodium chloride, 0.1 g magnesium sulfate, 2.5 g ammonium sulfate, 0.06 g bromothymol blue, 0.04 g propyl red, 0.0, 2.0, 6.0, 8.0, 10.0 g tryptose, respectively, and 15 g agar were dissolved in 1 liter of distilled water. The medium was sterilized at 121° C. and 15 p.s.i. for 15 minutes and then poured into pre-sterilized 45 mm petri dishes, and allowed to solidify.

VI. Variable glucose supplementation experiments

Glucose-supplementation of mX media enhances both colony size and catabolite repression of b-galactosidase in coliform strains. Thus there is an enlargement of the colorless b-galactosidase-negative outer region around the blue/green center of the colony. This results in a more striking "bullseye" appearance in the non-E. coli coliforms. The table below shows the increase in colony size resulting from glucose supplementation. The increase is generally proportional to glucose concentration, although the rough measurements below do not show the smaller incremental size increases at the higher glucose concentrations.

Colony diameter of E. coli and coliform strains on glucose supplemented mX agar

| Percent glucose | E. coli | K. pnuemoniae | C. freundii |
| --- | --- | --- | --- |
| 0.0 mm | 1.01 mm | 1.8 mm | 1.0 mm |
| 0.05 | 2 mm | 2.2 mm | 1.2 mm |
| 0.1 | 2+ mm | 2–3 mm | 1–2 mm |
| 0.15 | 2–3 mm | 2–3 mm | 1–2 mm |
| 0.2 | 2–3 mm | 2–3 mm | 1–2 mm |
| 0.4 | 2–3 mm | 2–3 mm | 1–2 mm |
| 0.6 | 2–3 mm | 2–3 mm | 1–2 mm |

Although both E. coli and other coliform bacteria grown on XGal containing mX agar will grow as blue colonies, non-coli coliform colonies will be able to metabolize adonitol and cellobiose and will therefore be locally catabolite repressed for b-galactosidase at the quickly growing outer region of the colony. This outer region will subsequently appear colorless or white surrounding the blue center of the colony. Rapid metabolic breakdown of adonitol and cellobiose also causes an increase in the local acidity at the outer region. When the pH indicator bromothymol blue is present in mX medium, the outer region will become yellow colored.

Addition of a low level of glucose enhances the catabolite repressive effect on non-coli coliform colonies, while still not significantly decreasing βgalactosidase activity at E. coli colonies. The table below shows that as sugar breakdown at non-coli coliform colonies increases (outer region becomes yellow colored), β-galactosidase activity simultaneously decreases (absence of blue color at outer region). Note that under certain conditions, both blue and yellow are present, creating the color green.

Higher levels of glucose (above 0.4% in this experiment) interfered with the expression of E. coli β-galactosidase activity.

Repression of XGal hydrolysis by glucose supplementation in mX medium

| Percent glucose | E. coli | K. pnuemoniae | C. freundii |
| --- | --- | --- | --- |
| 0.0 | dark blue only | green center, light green outer region | blue, very small lighter blue outer region |

-continued

| Percent glucose | E. coli | K. pnuemoniae | C. freundii |
|---|---|---|---|
| 0.05 | dark blue only | green center, pale outer region | green center, small light green outer region |
| 0.1 | dark blue only | green center, pale outer region | green center, light green-yellow outer region |
| 0.15 | dark blue only | green center, yellow outer region | green center, yellow outer region |
| 0.2 | dark blue only | green center, yellow outer region | green center, yellow outer region |
| 0.4 | gray | yellow only | green center, yellow outer region |
| 0.6 | gray | yellow only | green center, yellow outer region |

Glucose supplemented formulations of mX:
Glucose supplemented mX media 14a–14g 50 mg XGal predissolved in 0.1 ml dimethylformamide, 0.1 g IPTG, 5 g adonitol, S g cellobiose, 2.9 g sodium chloride, 10.0 g tryptose, 0.1 g magnesium sulfate, 2.5 g ammonium sulfate, 0.06 g bromothymol blue, 0.04 g propyl red, 0.0, 0.5, 1.0, 1.5, 2.0, 4.0 and 6.0 g glucose, respectively, and 15 g agar were dissolved in 1 liter of distilled water. The medium was sterilized at 121° C. and 15 p.s.i. for 15 minutes and then poured into pre-sterilized 45 mm petri dishes, and allowed to solidify.

VII. mX medium 15: supplemented with tryptophan
mX medium 15

50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, and 1.0 g tryptophan were dissolved in 1 liter of distilled water. The medium was dispensed into capped test tubes and sterilized at 121° C. and 15 p.s.i. for 15 minutes.

VIII. Ambient temperature incubation

Control strains *E. coli* ATCC 25922 and *Klebsiella pnuemoniae* TC 249 were used in an mX membrane filtration experiment with ambient temperature (18–25° C.) incubation. Experimental procedure was the same as that previously described. Generally, the appearance of colonies was similar to that of the 35° C. incubation experiments, but colonies were smaller due to the slower growth rate of bacteria at ambient temperatures. Results are as follows:

Colony appearance of *E. coli* and *K. pnuemoniae*, and *C. freundii* on mX agar with various pH indicators

| pH indicator[1] | Colony appearance of E. coli ATCC 25922 | Average colony size | Colony appearance of Klebsiella pnuemoniae[2] TC 249 | Average colony size |
|---|---|---|---|---|
| neutral red | dark-blue center only | 1 mm | light-blue center, light-red outer region | 1.5 min |
| brilliant yellow | dark-green only, yellow filter[3] | 1 mm | green center, pale yellow outer region, yellow filter[3] | 1.5 mm |
| bromothymol blue | blue-green only, yellow filter[3] | 1 mm | green center, pale yellow outer region, yellow filter[3] | 1.5 mm |
| alizarin | blue only | 0.5 mm | almost colorless | 1.5 mm |
| propyl red | blue only, pink-orange filter[3] | 1 mm | light-blue center, large colorless outer region, pink-orange filter[3] | 1.5 mm |
| phenol red | blue only | | 1 mm | light-blue center, large colorless outer region | 1.5 mm |
| bromothymol blue + indigo carmine (0.02 g/l) | dark green only, on light green filter[3] | 1 mm | light-green center, large, pale yellow outer region, yellow filter[3] | 1.5 mm |
| bromothymol blue + evans blue 0.009 g/l | dark blue-green only, green filter[3] | 1 mm | light-green center, large, pale yellow-green outer region, green filter[3] | 1.5 mm |
| bromothymol blue + propyl red (0.03 g/l) | dark green only, pink filter[3] | 1 mm | light-green center, large, pale yellow outer region, red filter[3] | 1.5 mm |

[1]The concentration of pH indicators was between 0.04–0.06 g/l unless otherwise specified. Initial pH of agar was 7.0–7.2.
[2]A commonly occurring coliform.
[3]Membrane filters were colored by some pH indicators.

IX. Fecal coliform temperature incubation

Control strains *E. coli* ATCC 25922 and *Klebsiella pnuemoniae* TC 249 were used in an mX membrane filtration experiment with fecal coliform temperature (44.5±0.2° C.) incubation. Experimental procedure was the same as that previously described, except plates were placed inside waterproof plastic bags (Whirlpak), and completely submerged in a 44.5° C. water bath for 18–24 hours. Generally, the appearance of colonies was similar to that of the 35° C. incubation experiments, but colonies were smaller due to the slower growth rate under the thermal stress of a high temperature incubation. Results are as follows:

Colony appearance of *E. coli* and *K. pnuemoniae*, and *C. freundii* on mX agar with various pH indicators

| pH indicator[1] | Colony appearance of E. coli ATCC 25922 | Average colony size | Colony appearance of Klebsiella pnuemoniae[2] TC 249 | Average colony size |
|---|---|---|---|---|
| neutral red | dark-blue center only | 1 mm | light-blue center, light-red outer region | 1.2 mm |
| brilliant yellow | dark-green only, yellow filter[3] | 1 mm | green center, pale-colored outer region, yellow filter[3] | 1.2 mm |
| bromothymol blue | blue-green only, yellow filter[3] | 1 mm | green center, pale colored outer region, yellow filter[3] | 1.2 mm |
| alizarin | blue only | — mm | almost colorless | 1.0 mm |
| propyl red | blue only, pink-orange filter[3] | 1 mm | light-blue center, large colorless outer region, pink-orange filter[3] | 1.2 mm |

-continued

| pH indicator[1] | Colony appearance of E. coli ATCC 25922 | Average colony size | Colony appearance of Klebsiella pnuemoniae[2] TC 249 | Average colony size |
|---|---|---|---|---|
| phenol red | blue only | 1 mm | light-blue center, large colorless outer region | 1.2 mm |
| bromothymol blue + indigo carmine (0.02 g/l) | dark green only, on light green filter[3] | 1 mm | light-green center, large, pale yellow outer region, yellow filter[3] | 1.2 mm |
| bromothymol blue + evans blue (0.009 g/l) | dark blue-green only, green filter[3] | 1 mm | light-green center, large, pale yellow-green outer region, green filter[3] | 1.2 mm |
| bromothymol blue + propyl red (0.03 g/l) | dark green only, pink filter[3] | 1 mm | light-green center, large, pale yellow outer region, red filter[3] | 1.2 mm |

[1]The concentration of pH indicators was between 0.04–0.06 g/l unless otherwise specified. Initial pH of agar was 7.0–7.2.
[2]A commonly occurring coliform.
[3]Membrane filters were colored by some pH indicators.

X. Chlorinated Sewage Influent

Samples of primary sewage influent were collected in sterile capped polypropylene bottles from local sewage treatment plants, and kept on ice during transportation. As soon as possible, samples were vacuum filtered through Whatman 40 filter paper to remove large particles, and enumerated for *E. coli* using the Standard Methods' 1) mTEC and 2) mENDO transferred to NA-MUG membrane filtration methods. The sample was then chlorinated at approximately 2.5 mg/l chlorine residual for 20 minutes at room temperature. Chlorine residual was monitored by the Standard Methods' DPD colorimetric method. The chlorinated sample was then reenumerated with mTEC and mENDO to NA-MUG for *E. coli* to verify 2–4 logs of bacterial killing, and to allow for a dilution estimate based on the number of remaining *E. coli* in the chlorinated sample. 100 ml volumes of chlorinated sample were used for membrane filtration, and counts of *E. coli* and total coliforms were taken for mX, mENDO to NA-MUG, and mTEC (*E. coli* only) media. Results are listed in the table below.

*Comparison of mX to the Standard Membrane Filtration Methods for detection of *E. coli* and coliforms

| Sample no. | mENDO (coliform) | mX (coliform) | mX (E. coli) | mENDO transferred to NA-MUG (E. coli) | mTEC Transferred to VREASE regent pad (E. coli) |
|---|---|---|---|---|---|
| 1 | 100 | 98 | 9 | 8 | 1 |
| 2 | 114 | 120 | 10 | 10 | 0 |
| 3 | 95 | 113 | 8 | 10 | 2 |
| 4 | 105 | 99 | 11 | 10 | 1 |
| 5 | 110 | 106 | 10 | 11 | 0 |
| 6 | 108 | 115 | 10 | 7 | 0 |
| 7 | 102 | 97 | 9 | 8 | 1 |
| 8 | 94 | 103 | 10 | 7 | 0 |
| 9 | 112 | 118 | 8 | 10 | 1 | mX medium 16 for Chlorination, and Specificity, Protocol, EPA 50 mg XGal predissolved in 0.1 ml dimethylformamide, 0.1 g IPTG, 5 g adonitol, 5 g cellobiose, 2.9 g sodium chloride, 10.0 g tryptose, 0.1 g magnesium sulfate, 2.5 g ammonium sulfate, 0.06 g bromothymol blue, 0.04 g propyl red, 1.5 g glucose, 0.1 g sodium lauryl sulfate, and 15 g agar were dissolved in 1 liter of distilled water. The medium was sterilized at 121° C. and 15 p.s.i. for 15 minutes and then poured into pre-sterilized 45 mm petri dishes, and allowed to solidify.

mX 16 is the most preferred formulation of mX media, and is used in the ambient and high temperature runs.

XI. Specificity testing

18 Surface and Groundwater samples were collected and enumerated for *E. coli* and coliforms using the mX method for membrane filtration. Representative colonies from each sample run were selected at random for bacterial identification using the API20E system for enterobacteriaciae. Results are show in the table below.

Comparison of mX with the Standard Coliform and *E. coli* Tests on Surface and Groundwaters ;

| Origin of strain | Colony appearance | Bacterial identification |
|---|---|---|
| surface | dark blue only | Escherichia coli |
| surface | light blue center, white outer region | Citrobacter freundii |
| surface | blue only | Escherichia coli |
| source | green center, white outer region | Klebsiella pnuemoniae |
| source | yellow only | Aeromonas hydrophila |
| surface | white only | Pasteurella multicida |
| surface | Dark blue only | Escherichia coli |
| surface | blue-green center, white outer region | Klebsiella oxytoca |
| source | light blue center, white outer region | Enterobacter cloacae |
| surface | light blue center, white outer region | Serratia marcesens |
| surface | light blue center, white outer region | Enterobacter sakazakii |
| source | light blue center, white outer region | Citrobacter freundii |
| surface | Dark blue only | Escherichia coli |
| surface | Dark blue only | Escherichia coli |
| source | blue-green center, white outer region | Klebsiella oxytoca |
| surface | green center, white outer region | Klebsiella pnuemoniae |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting coliform bacteria and *E. coli*, said method comprising the steps of:
   (a) contacting a bacterial colony with a β-D-galactosidase substrate;
   (b) contacting said bacterial colony with a first carbon source metabolizable by a plurality of coliform species but not metabolizable by *E. coli*, wherein metabolism of said first carbon source provides a reaction product at said colony;
   (c) detecting a first reaction product signal of said β-D-galactosidase substrate at said colony;

(d) detecting a second reaction product signal of said carbon source at said colony;

wherein the absence of both said first and second reaction product signals indicates the presence of non-coliform bacteria in said colony, the presence of said first and absence of said second reaction product signal indicates the presence of *E. coli* in said colony, and the presence of said first and second reaction product signals indicates the presence of non-*E. coli* coliform bacteria in said colony.

2. A method according to claim 1 wherein, said bacterial colony comprises a first region and a second region, said second region being located outwardly of said first region; and said second reaction product signal comprises a lower intensity first reaction product signal at said second region as compared with said first region.

3. A method according to claim 1, wherein said bacterial colony comprises a first region and a second region, said second region being located outwardly of said first region; and said second reaction product signal comprises a lower localized pH at said second region as compared with said first region.

4. A method according to claim 2, wherein said method further comprises the step of:

contacting said bacterial colony with a second carbon source different from said first carbon source in an amount sufficient to reduce the intensity of said lower intensity first reaction product signal at said second region as compared with said first region.

5. A method according to claim 2, wherein, prior to said detecting step said bacterial colony is contacted with a reagent which limits bacterial growth or incubated under conditions which limit bacterial growth, said reagent being at least one of azide, cyanide, a semitoxic dye, antibiotic, urea and guanidine, said conditions being starvation for at least one of a nitrogen source, phosphate and salts, and the intensity of said lower intensity first reaction product signal at said second region is further reduced as compared with said first region.

6. A method according to claim 1, wherein said first and second reaction product signals are detected by color changes.

7. A method according to claim 1, wherein said first carbon source comprises a carbohydrate.

8. A method according to claim 1, wherein said carbon source comprises adonitol, esculin, salicin, amygdalin, or cellobiose.

9. A method according to claim 1, wherein said β-D-galactosidase substrate is chromogenic and provides an insoluble reaction product.

10. A method according to claim 1, wherein said β-D-galactosidase substrate is X-GAL (5-bromo-4-chloro-3-indolyl-β-D-galactopyranoside).

11. A method according to claim 1, wherein said colony is on a microporous filter.

12. A method according to claim 1, wherein prior to said contacting steps, said method further comprises incubating a bacterium under conditions sufficient to grow said bacterium into said bacterial colony, wherein said incubating is performed at ambient temperature.

13. A method according to claim 1, wherein after said contacting steps, said method further comprises contacting said bacterial colony with a reagent capable of producing a color change at said colony when said second reaction product is present.

14. A method according to claim 1, wherein after said contacting steps, said method further comprises contacting said colony with a pH indicator or a tetrazolium dye capable of producing a color change at said colony when said second reaction product is present.

15. A method according to claim 12, wherein said conditions provide for the repression of tryptophanase activity in non-*E. coli* bacteria, said method further comprising the steps of:

(f) contacting said bacterial colony with a tryptophanase substrate;

(g) detecting a third reaction product signal of said tryptophanase substrate at said colony;

wherein the presence of said third reaction product signals indicates the presence of *E. coli* in said colony, and the absence of said third reaction product signal indicates the absence of *E. coli* bacteria in said colony.

16. A method according to claim 15, wherein said conditions include contacting said bacterial colony with said first carbon source in an amount sufficient to repress tryptophanase activity in said non-*E. coli* bacteria, or incubating at a temperature between 40 and 45° C.

17. A sterile medium for use in detecting coliform bacteria and *E. coli*, said medium comprising:

(a) a β-D-galactosidase substrate;

(b) a carbohydrate metabolizable by a plurality of coliform species but not metabolizable by *E. coli*; and (c) salts.

18. A medium according to claim 17 wherein said β-D-galactosidase substrate is chromogenic and provides an insoluble reaction product and said carbohydrate is adonitol, cellobiose or amygdalin.

19. A kit for detecting coliform bacteria and *E. coli* on a microporous filter, said kit comprising:

(a) a sterile, premeasured amount of a medium according to claim 17, and (b) a microporous filter.

20. A kit according to claim 19 wherein said β-D-galactosidase substrate is chromogenic and provides an insoluble reaction product and said carbohydrate is adonitol, cellobiose, esculin, salicin or amygdalin.

* * * * *